(12) United States Patent
Tucek et al.

(10) Patent No.: US 8,439,959 B2
(45) Date of Patent: May 14, 2013

(54) FULL-BODY LASER SCANNER AND METHOD OF MAPPING AND CONTOURING THE BODY

(75) Inventors: Kevin Tucek, McKinney, TX (US); Charles Shanks, McKinney, TX (US)

(73) Assignee: Erchonia Corporation, McKinney, TX (US)

( * ) Notice: Subject to any disclaimer, the term of this patent is extended or adjusted under 35 U.S.C. 154(b) by 263 days.

(21) Appl. No.: 12/870,002

(22) Filed: Aug. 27, 2010

(65) Prior Publication Data

US 2010/0324426 A1    Dec. 23, 2010

Related U.S. Application Data

(63) Continuation-in-part of application No. 10/976,581, filed on Oct. 29, 2004, now Pat. No. 7,922,751.

(60) Provisional application No. 61/237,795, filed on Aug. 28, 2009.

(51) Int. Cl.
*A61N 5/06* (2006.01)

(52) U.S. Cl.
USPC ....... 607/89; 607/88; 606/9; 606/10; 128/898

(58) Field of Classification Search ................ 606/3–12, 606/20–28, 32; 607/88–93, 96–112; 128/898
See application file for complete search history.

(56) References Cited

U.S. PATENT DOCUMENTS

| | | |
|---|---|---|
| 3,023,662 A | 3/1962 | Hicks |
| 4,729,372 A | 3/1988 | L'Esperance |
| 4,733,660 A | 3/1988 | Itzkan |
| 4,767,930 A | 8/1988 | Stieber et al. |
| 5,046,494 A | 9/1991 | Searfoss et al. |
| 5,284,477 A | 2/1994 | Hanna et al. |
| 5,413,555 A | 5/1995 | McMahan |
| 5,461,473 A | 10/1995 | Pratt |

(Continued)

FOREIGN PATENT DOCUMENTS

JP    2003174922    6/2003

OTHER PUBLICATIONS

Canadian Intellectual Property Office, Requisition by the Examiner in Accordance with Subsection 30(2) of the Patent Rules, Jul. 14, 2010, Canada.

(Continued)

*Primary Examiner* — Ahmed Farah
(74) *Attorney, Agent, or Firm* — Etherton Law Group, LLC; Sandra L. Etherton (57) ABSTRACT

A full-body non-invasive laser scanner for mapping or measuring a patient's body and for treating a patient's body with laser energy comprises a patient support, one or more laser devices, a laser guidance system, a control center, and optionally feedback sensors. The patient support aids in maintaining body alignment during treatment, and the laser devices are moveably positioned on a laser guidance system such that they can be driven about a stationary patient. To map and contour a patient's body, the patient aligns himself on the patient support. With the control center, an operator chooses whether to map, contour, or map and contour the patient's body either manually or according to preprogrammed treatment protocols. The carriage assembly translates and the laser devices apply laser energy to the surfaces of the patient's body according to the chosen protocol. Feedback sensors provide data for mapping the contours of the patient's body.

20 Claims, 7 Drawing Sheets

U.S. PATENT DOCUMENTS

| | | | |
|---|---|---|---|
| 6,013,096 A | 1/2000 | Tucek | |
| 6,094,760 A * | 8/2000 | Nonaka et al. | 5/601 |
| 6,208,673 B1 | 3/2001 | Miyake | |
| 6,267,779 B1 | 7/2001 | Gerdes | |
| 6,358,272 B1 | 3/2002 | Wilden | |
| 6,605,079 B2 | 8/2003 | Shanks et al. | |
| 6,746,473 B2 | 6/2004 | Shanks et al. | |
| 7,118,588 B2 | 10/2006 | Tucek et al. | |
| 7,648,498 B2 * | 1/2010 | Hempel | 606/33 |
| 7,869,562 B2 * | 1/2011 | Khamene et al. | 378/20 |
| 2001/0053907 A1 * | 12/2001 | Ota | 606/10 |
| 2002/0111656 A1 | 8/2002 | Lach | |
| 2002/0123743 A1 | 9/2002 | Shanks et al. | |
| 2002/0123781 A1 | 9/2002 | Shanks et al. | |
| 2003/0109860 A1 | 6/2003 | Black | |
| 2003/0216795 A1 * | 11/2003 | Harth et al. | 607/88 |
| 2004/0123472 A1 | 7/2004 | Wu | |
| 2004/0162549 A1 | 8/2004 | Altshuler | |
| 2004/0210214 A1 | 10/2004 | Knowlton | |
| 2005/0197681 A1 * | 9/2005 | Barolet et al. | 607/86 |
| 2005/0203594 A1 | 9/2005 | Lim et al. | |
| 2006/0020259 A1 * | 1/2006 | Baumeister et al. | 606/5 |
| 2008/0058906 A1 * | 3/2008 | Spangler et al. | 607/89 |
| 2008/0194942 A1 * | 8/2008 | Cumpson et al. | 600/415 |
| 2009/0012586 A1 * | 1/2009 | Kepecs | 607/89 |
| 2009/0024142 A1 * | 1/2009 | Ruiz Morales | 606/130 |
| 2009/0171266 A1 | 7/2009 | Harris | |
| 2011/0026685 A1 * | 2/2011 | Zilberstein et al. | 378/197 |
| 2011/0172746 A1 * | 7/2011 | Porter | 607/89 |

OTHER PUBLICATIONS

State Intellectual Property Office, P.R. China, First Office Action, Jun. 4, 2010, Peoples Republic of China.

Korean Intellectual Property Office, Notice of Request for Submission of Argument, Oct. 15, 2010, Korea.

European Patent Office, Communication pursuant to Article 94(3) EPC, Feb. 16, 2009, Netherlands.

Response to First Office Action of State Intellectual Property Office, P.R. China, Sep. 30, 2010, China.

International Searching Authority, European Patent Office, International Search Report and Written Opinion, Jan. 28, 2008, Netherlands.

Israel Intellectual Property Office, Official Notification, Oct. 26, 2010, Israel.

Response to Communication pursuant to Article 94(3) EPC dated Feb. 16, 2009, Jun. 8, 2009, United Kingdom.

* cited by examiner

FULL-BODY LASER SCANNER AND METHOD OF MAPPING AND CONTOURING THE BODY

CROSS-REFERENCE TO RELATED APPLICATIONS

This application claims the benefit of provisional application No. 61/237,795, filed Aug. 28, 2009 and is a continuation-in-part-of co-pending U.S. application Ser. No. 10/976,581 filed Oct. 29, 2004.

FIELD OF INVENTION

This invention relates to a full-body laser scanner and a method for non-invasive shaping and contouring of a human body by external means. In particular, this invention relates to the application of laser energy and the recording of proximity feedback to map the contours of a patient's full body and treat a patient's full body.

BACKGROUND

There is a great demand to contour the body and reduce cellulite. Cellulite is often described as skin with ripples or dimples or as skin having a cottage cheese or orange-peel texture. Cellulite mainly affects women, although some men also suffer from cellulite. Typically, cellulite is most prevalent on their thighs, hips and buttocks, but it also can be found on the breasts, lower abdomen and upper arms as well. In an effort to reduce cellulite, many people resort to one of three treatment options: liposuction or similar methods of removing fat, vigorous massage, or cellulite creams. Unfortunately, none of these options have been effective at actually reducing cellulite. Additionally, each of these options requires distinct treatments for each area requiring treatment.

Cellulite is the herniation of superficial and deep fat into the dermis. Latest research suggests that longitudinal fibers or cords of connective tissue fascia, which is comprised of collagen, is progressively weakened by estrogen. The fascia hardens and loses its ability to contain the fat mass that is normally contained in chambers separated by septa of connective tissue. The weakened fascia allows the fat to move upward and push into the dermis. As the connective tissue gives way the fat mass is free to expand, leading to a wavy or dimpled skin appearance commonly called cellulite. Unfortunately, cellulite does not respond well to weight loss, exercise, creams, or surgical liposuction.

In an effort to reduce cellulite, many sufferers try to remove the underlying fat through surgical procedures such as liposuction or through liposuction alternatives. Liposuction involves suctioning excess adipose tissue from the body of a patient. Generally, adipose tissue is connective tissue comprising collagen fibers, reticular fibers, non-cellular material and adipocytes. Adipocytes, the fat cells, are enclosed membranes filled with globules of triglycerides. In normal fat the adipocytes have regular contours and form into grapelike clusters. The intracellular fat is relatively fluid and, if the membrane is pierced, will flow out of the cell into the interstitial space. The interstitial space includes the connective tissue as well as nerves, blood vessels, and lymphatics, among other substances.

While liposuction is effective at removing fat, traditional liposuction has not been effective in reducing cellulite and may actually make the cellulite appear worse. Additionally, traditional liposuction carries undesirable risks and side effects because it involves inserting a narrow tube, or cannula, through a tiny incision in the skin into the subcutaneous fatty tissue and repeatedly pushing and pulling through the fat layer, separating and puncturing the fat cells and suctioning them out. The procedure can damage nerves, lymphatics and vasculature in the surrounding area, often resulting in significant loss of blood as the blood is vacuumed out with the fat and the formation of seroma due to damaged lymphatic channels. In addition, the post-procedure recovery period is long and often accompanied by a great deal of inflammation, bruising and concomitant pain. Finally, each area needing treatment must be treated separately with liposuction.

Improvements to liposuction have somewhat diminished the danger and post-operative side-effects of traditional liposuction. For example, the tumescent technique uses injections of dilute amounts of an anesthetic and a vasoconstrictor to reduce pain and lessen blood loss. Further developments include using low energy laser therapy in conjunction with suction of the fat cells, as disclosed in U.S. Pat. No. 6,605,079, issued to one of the inventors of this method and incorporated herein. Low level laser therapy (LLLT) has been used successfully post-operative to liposuction to reduce inflammation and pain. Despite the improvements, however, liposuction remains invasive and ineffective at treating cellulite and continues to require separate procedures at each distinct treatment area.

Non-invasive methods of reducing fat have also proven ineffective at reducing cellulite. In general, non-invasive methods are preferred because they minimize trauma to the patient, reduce the risk of infection, and speed up recovery time, among other reasons. Such non-invasive methods include subjecting a patient to electromagnetic energy, such as microwave, ultrasound or radio frequency radiation. These procedures are disadvantageous, however, because they utilize such high energy sources that they heat the surrounding tissue, which can result in damage to the tissue and pain. Again, recovery time is significant, and these methods are not effective at reducing cellulite.

A less traumatic non-invasive method of reducing fat is described U.S. Patent Publication 2005/0203594. U.S. Patent Publication 2005/0203594 discloses the use of low-level laser energy applied externally to the patient to release at least a portion of the intracellular fat into the interstitial space, wherein the released fat and damaged fat cells are removed from the patient's body through one or more of the patient's normal bodily systems. While effective for fat reduction, it would be desirable to apply this method to a broad area of the patient for faster and more efficient treatment.

It would be desirable to reduce treatment time for contouring a patient's body. It would also be desirable to map or measure a patient's full body to enhance treatment options. Therefore, an object of this invention is to provide a full-body non-invasive laser scanner for mapping and treating a patient. Another object of this invention is to provide a method of treating a patient's body with laser energy using a full-body laser scanner.

SUMMARY OF THE INVENTION

This invention is a full-body non-invasive laser scanner for mapping or measuring a patient's body contours and for treating a patient's body with laser energy. The full-body laser scanner comprises a patient support, one or more laser devices, a laser guidance system, a control center, and optional feedback sensors. The patient support can be a seat, a platform, a bed, or another structure that supports a patient and aids in maintaining body alignment during treatment. The laser devices are directed toward the patient and are moveably positioned on a laser guidance system such that they can be driven about a stationary patient for treatment and mapping. In a first embodiment, the laser guidance system is a linear guidance system that supports upper and lower laser devices and feedback sensors. The lasers and feedback sensors are translated with a carriage assembly that translates along a guiderail substantially parallel to the patient. In second and third embodiments, the laser guidance system is an orbital guidance system comprising an orbital guide ring that partially or fully surrounds a patient and supports one or more laser devices and feedback sensors. Further, the orbital guide ring is fixed to a carriage assembly that translates vertically substantially parallel to a patient who is seated or standing. The control center includes a display, an input device and control circuitry to individually operate the lasers, the feedback sensors, the laser guidance system, and the patient support of each embodiment.

To map and contour a patient's body with the full-body laser scanner, the patient is aligned on the patient support. With the control panel, an operator chooses whether to map, contour, or map and contour the patient's body. The operator chooses any preprogrammed treatment protocols or manually controls the carriage's movement and the lasers. The carriage assembly translates in either one continuous translation or with several back and forth translations of various amounts. While the carriage assembly translates, the laser devices apply laser energy to the surfaces of the patient's body. Using sensors, the full-body laser scanner records and maps the contours of the patient's body and identifies targeted areas of the body for laser treatment. Alternately, the operator manually identifies targeted areas of the body for laser treatment. Next, low-level laser energy is applied to the targeted areas of the patient's body to reduce cellulite and contour the body. Laser energy can also be applied according to treatment protocols for other laser applications.

DETAILED DESCRIPTION OF THE INVENTION

Figure 7:
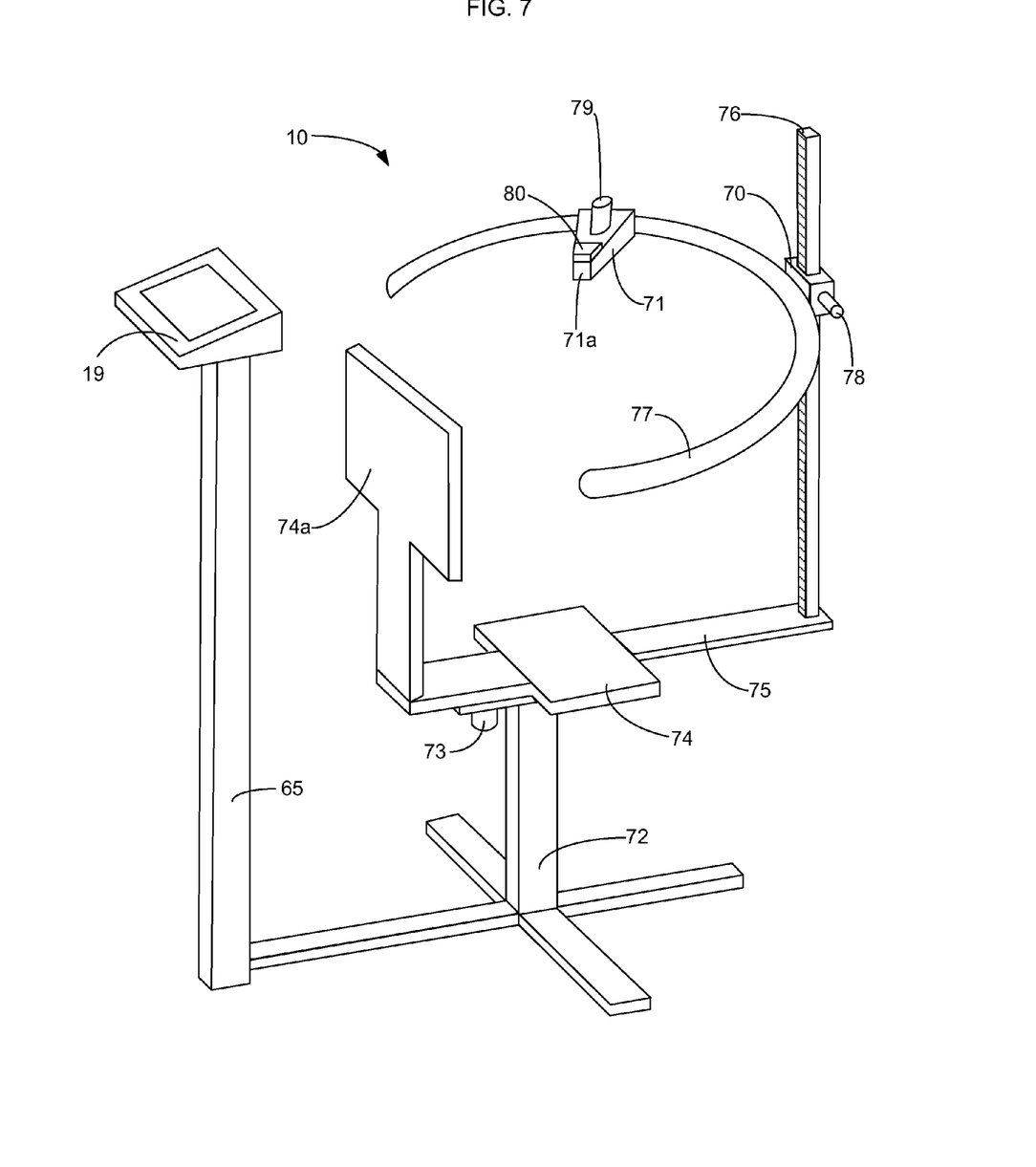
FIG. 7 is a perspective view of the second embodiment of the full-body laser scanner of the present invention.
Figure 8:
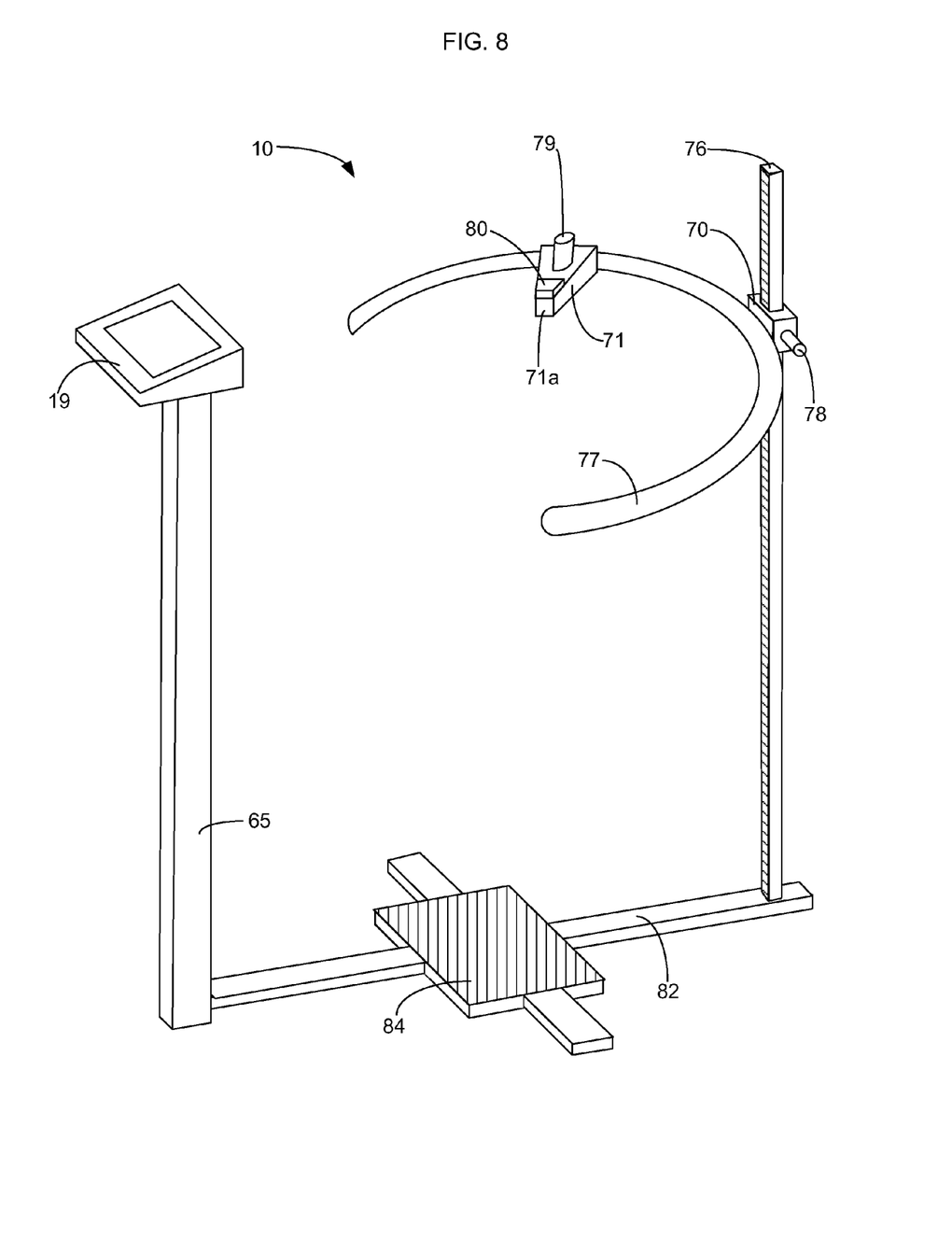
FIG. 8 is a perspective view of the third embodiment of the full-body laser scanner of the present invention.

The present invention is a full-body non-invasive laser scanner for mapping or measuring the contours of a patient's body and for treating a patient's body with laser energy. The full body scanner 10 comprises a patient support, a laser guidance system, one or more laser devices, and a control center and control system. Full body scanner 10 additionally optionally includes feedback sensors. FIGS. 1-5 illustrate a first embodiment of scanner 10 where the patient support is a base 12 with a bed. FIG. 7 illustrates a second embodiment of scanner 10 where the patient support is a chair 72, and FIG. 8 illustrates a third embodiment of scanner 10 where the patient support is a platform 82.

Referring to FIGS. 1-5, the first and preferred embodiment of scanner 10 comprises a table or base 12 with a bed preferably comprised of movable slats 14 and a laser guidance system 20. Base 12 can be any type of table or housing for a bed as long as base 12 is capable of partially or substantially supporting the weight of a patient, a part of a patient, or any other subject requiring laser energy treatment. As shown in FIGS. 1-4, base 12 is a frame with four supporting legs 12a. Alternately, base 12 can comprise pedestals, corbels, shelf-supports, a wall, or any other support structure as is known in the art. The base or bed can also be adjustable such that a portion of it can be elevated and a portion not elevated, such that it can convert to a chair or lounge, or such that the entire bed is sloped.

The bed is positioned on base 12 to create a resting surface on which a patient can lay prone. As shown in FIGS. 1-5, the bed is a series of repositionable slats 14 resting in channels 13 formed in base 12. The base and movable slats permit a patient to be treated on one more sides without realignment. For example, when a patient lies on the slats 14 face up, his front is exposed above the slats 14 for laser treatment and his back is exposed for laser treatment through the moveable slats 14. Alternately, the bed can be any support structure capable of retaining a patient in the prone position that does not substantially interfere with the application of laser light at the treatment area resting on the bed. For example, the bed can be a transparent solid surface, a series of narrow transparent or non-transparent rods, or a taut mesh surface, as will be understood by someone skilled in the art. If the bed is comprised of supports that can be positioned and repositioned, preferably the supports, e.g. rods or slats, can be moved or translated to expose different regions on a patient depending on the treatment protocol. For example, a patient can lay prone on translating slats that can be positioned to expose the abdomen for abdominal laser treatments or positioned to expose thighs for laser treatments on the patient's thighs. The supports can be moved manually or a motor and control system can be operationally connected to the supports to automatically move them according to a given protocol. For this embodiment, the slats would not need to be transparent.

As shown in FIGS. 1-5, the laser guidance system of the first embodiment is a linear guidance system that comprises a carriage rail 15 and a carriage assembly 16. The carriage assembly 16 translates on carriage rail 15 and comprises an upper arm 17, a lower arm 18, and vertical stanchion 22. Lower arm 18 extends below the bed and supports a plurality of lower laser devices 28 that are directed toward the bed. Vertical stanchion 22 extends upwards from carriage rail 15 and connects to upper arm 17, which extends above the bed and supports a plurality of upper laser devices 27 that are directed toward the bed. A control system and control center 19 cooperates with carriage assembly 16 and can be mounted directly on stanchion 22, upper arm 17, or lower arm 18. Control system and center 19 operate a drive motor (not shown) housed within carriage assembly 16 to control the carriage assembly's movement on carriage rail 15. Control center 19 also individually operates the laser devices.

Carriage rail 15 and carriage assembly 16 can be any type of linear guidance system that facilitates linearly translating an object, such as a track roller linear guidance system. For example, carriage rail 15 can be a guideway with a track on which the carriage assembly 16 is supported and rolls. Alternatively, carriage rail 15 can be a belt or conveyer system along which carriage assembly 16 translates. Any type of linear guidance system can be substituted, as is known in the art.

Carriage assembly 16 translates along carriage rail 15 and can house a battery, control circuitry, and any other components necessary to facilitate the carriage's movement along the carriage rail. Carriage assembly 16 also can house any components necessary for operating any of the plurality of lasers. Carriage assembly 16 also cooperates with control center 19, which can be physically, electrically, or wirelessly connected to carriage assembly 16.

Upper arm 17 is connected to carriage assembly 16 by vertical stanchion 22 so that upper arm 17 translates as carriage assembly 16 translates. Upper arm 17 can be fixed to stanchion 22 or it can be moveably attached such that the height of upper arm 17 is adjustable. Alternately, upper arm 17 can connect directly to or be integral with carriage assembly 16. Vertical stanchion 22 extends upwards from carriage assembly 16 and transparent bed 14 as shown in FIGS. 1-4. Upper arm 17 then extends over and across the width of transparent bed 14 as shown in particular in FIG. 2. The portion of upper arm 17 that extends over and across transparent bed 14 supports one or more upper laser devices 27. Each upper laser device 27 is oriented so that laser energy is directed toward transparent bed 14. Preferably, upper arm 17 also includes a horizontal alignment guide 37 on which each of the upper laser devices 27 can be repositioned and a vertical alignment system (not shown) for individually raising and lowering each of the upper laser devices 27. For example, each upper laser device 27 also can be lowered toward the patient or raised toward upper arm 17 without interfering with the operation of the upper laser devices 27. Preferably, each of the upper laser devices 27 are controlled by the control system and control center and moved automatically with horizontal and vertical movement drive motors (not shown).

Lower arm 18 is integral with or connected either directly or indirectly to carriage assembly 16 so that lower arm 18 translates as carriage assembly 16 translates. Lower arm 18 extends below and across the width of bed 14 as shown in particular in FIG. 3. Lower arm 18 can also be height adjustable and can extend downwards from carriage assembly 16 to create more clearance between transparent bed 14 and lower arm 18 if needed. The portion of lower arm 18 that extends below and across transparent bed 14 supports one or more lower laser devices 28. Each lower laser device 28 is oriented so that laser energy is directed toward transparent bed 14. Preferably, lower arm 18 also includes a horizontal alignment guide 38 on which each of the lower laser devices 28 can be repositioned and a vertical alignment system (not shown) for individually raising and lowering each of the lower laser devices 28. For example, each lower laser device 28 also can be raised toward the patient or lowered toward lower arm 18 without interfering with the operation of the lower laser devices 28. Preferably, each of the lower laser devices 28 are controlled by the control center and moved automatically with horizontal and vertical movement drive motors (not shown).

Upper laser devices 27 and lower laser device 28 can be any laser device that provides low-level energy. A laser device that provides low-level energy is known in the art as a cold laser, such as the inventions described in U.S. Pat. Nos. 6,013,096 issued to Tucek and 6,746,473, issued to Tucek and Shanks. The preferred laser is a semiconductor diode emitting laser light in the red range of the spectrum, having wavelengths of about 635 nm. Other lasers known in the art for use in low-level laser therapy include Helium-Neon lasers having a 632 nm wavelength and semiconductor diode lasers with a broad range of wavelengths between 405-1500 nm. Diode lasers at 625 nm, 633 nm, 670 nm and 1064 nm (infrared) have been shown to work with varying degrees of success. The laser device may have one or more laser energy sources. Different therapy regimens require diodes of different wattages. The preferred laser diodes use less than one watt of power each to simultaneously facilitate fat reduction, treat post-operative inflammation, and treat post-operative pain. Diodes of various other wattages may also be employed to achieve the desired laser energy for the given regimen. Low-level lasers are available commercially.

Figure 1:
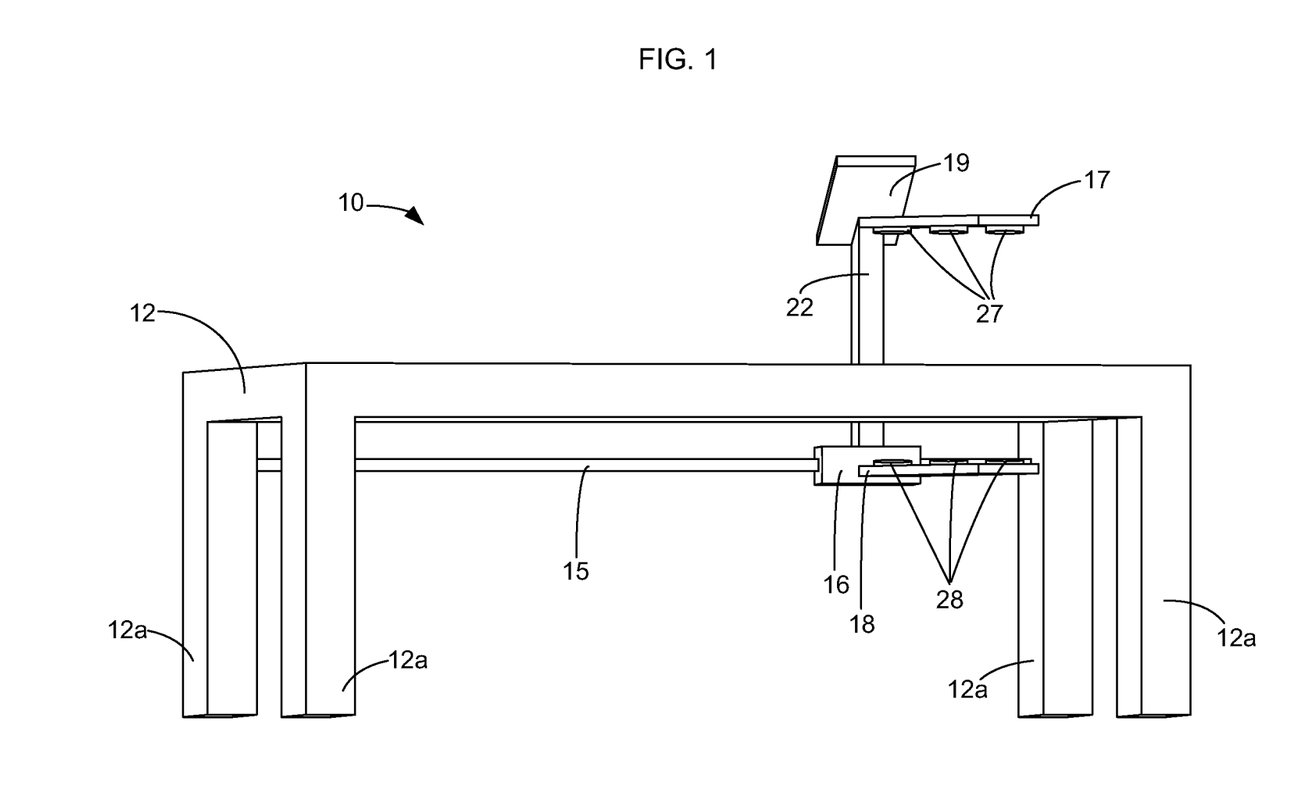
FIG. 1 is a perspective view of the first embodiment of a full-body laser scanner of the present invention.
Figure 2:
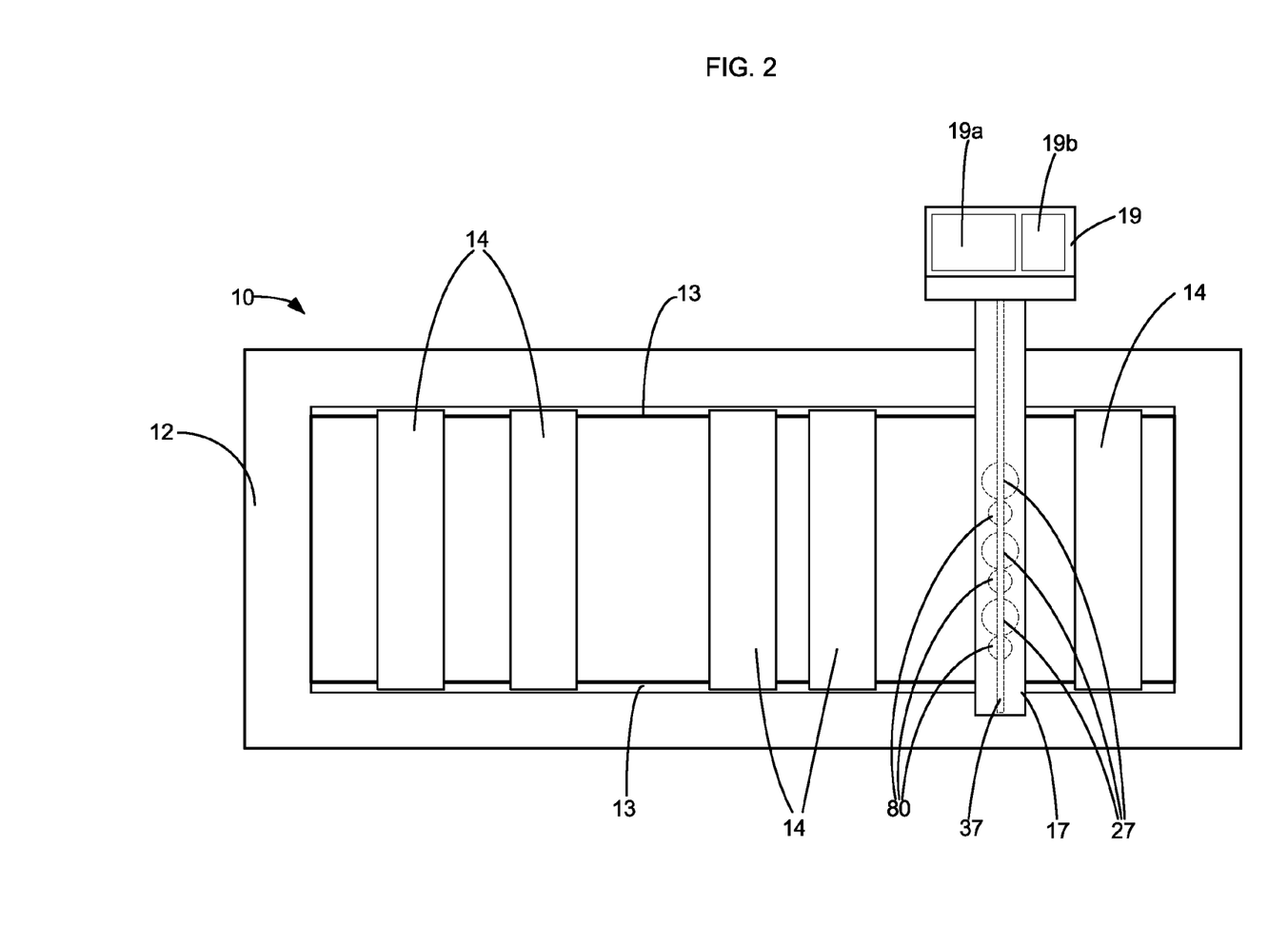
FIG. 2 is top view of the first embodiment of the full-body scanner of the present invention.
Figure 3:
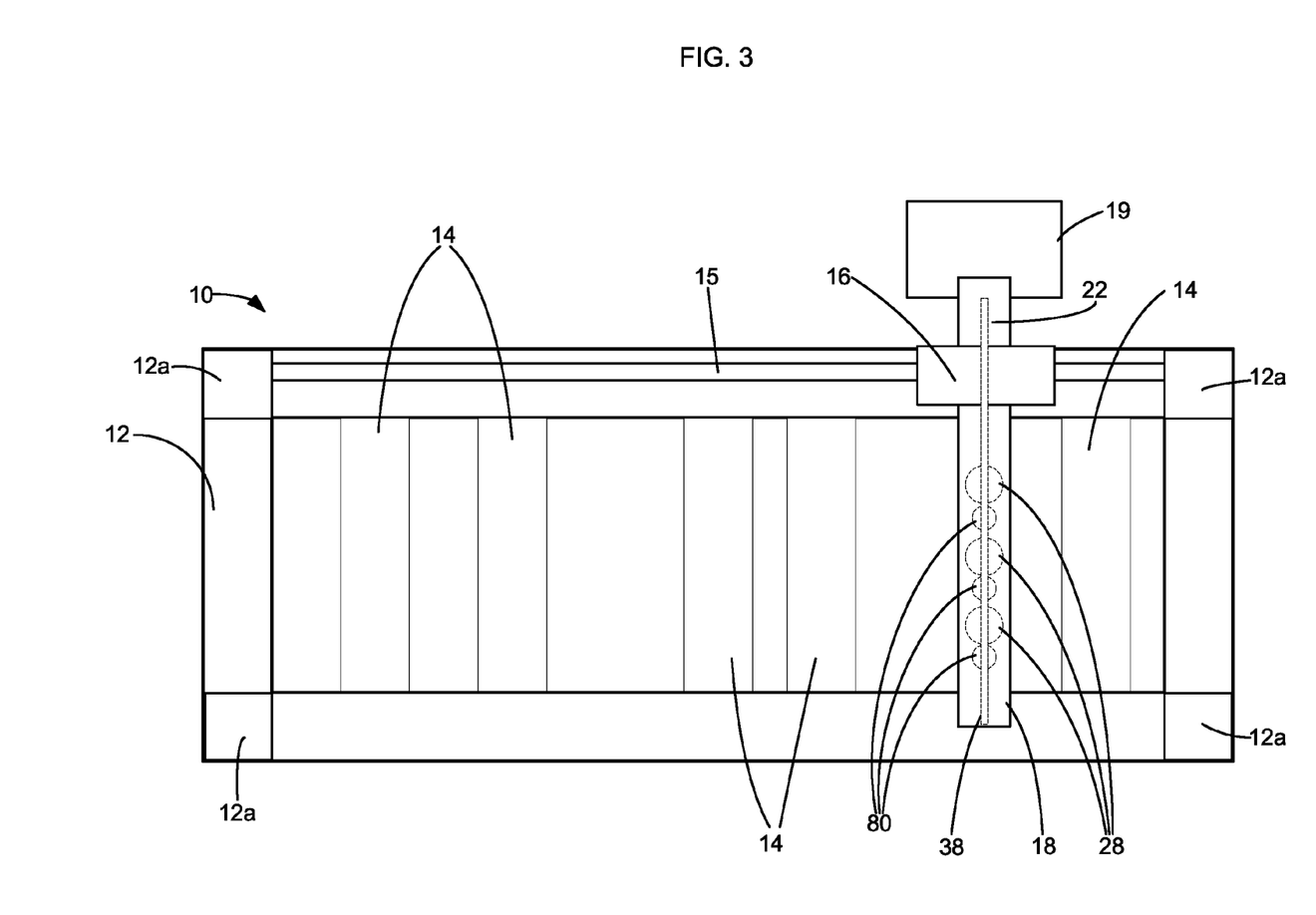
FIG. 3 is bottom view of the first embodiment of the full-body laser scanner of the present invention.
Figure 4:
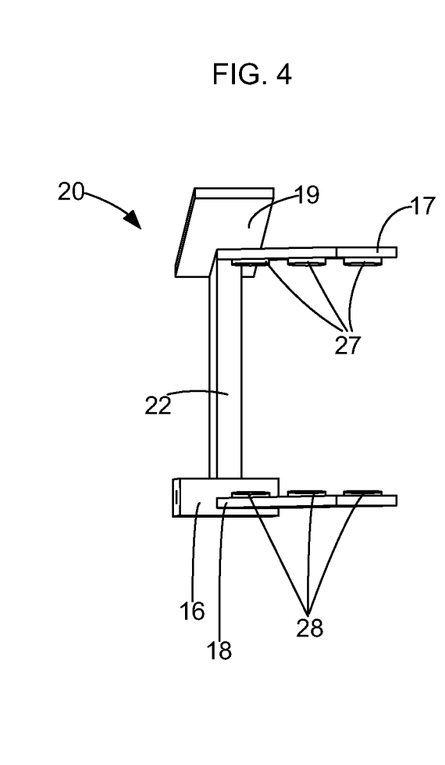
FIG. 4 is a perspective view of the laser guidance system of the first embodiment of the full-body laser scanner of the present invention.
Figure 5:
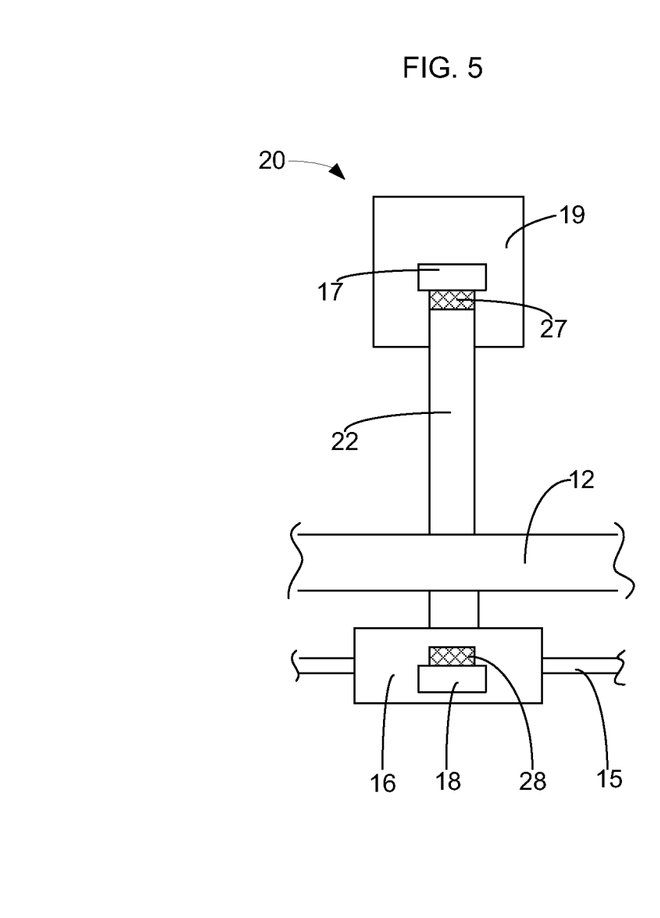
FIG. 5 is a side view of the laser guidance system of the first embodiment of the full-body laser scanner of the present invention
Figure 6:
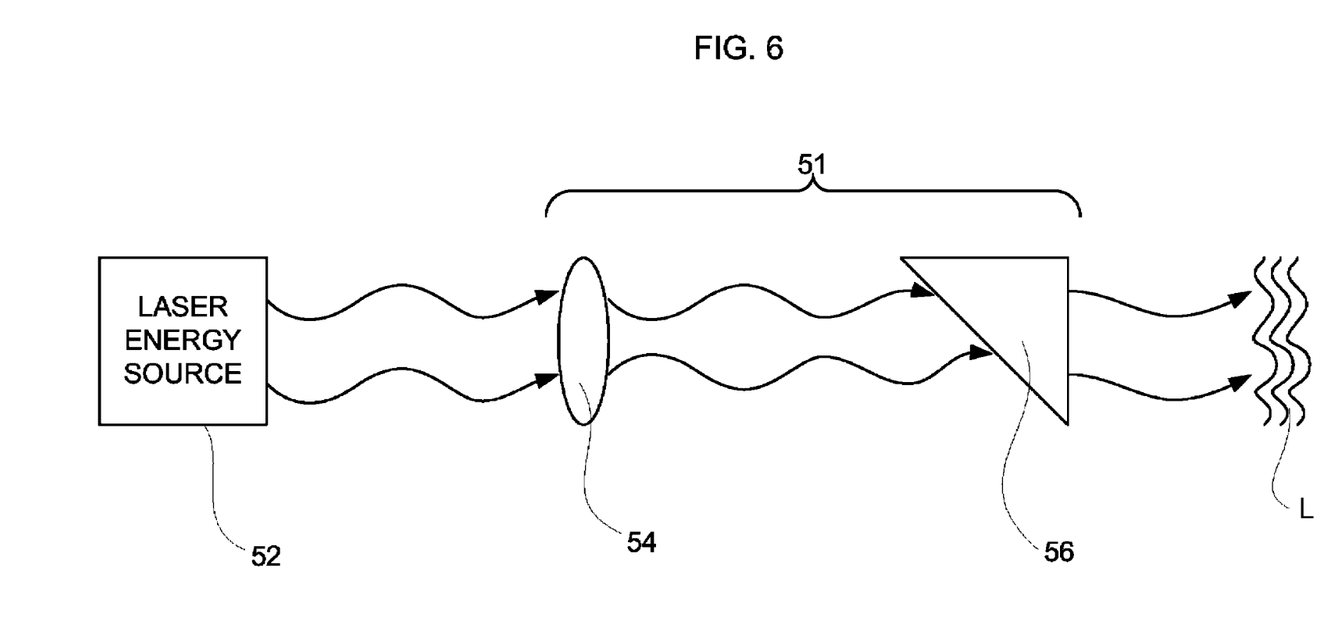
FIG. 6 is a schematic illustration of a laser and optical arrangement for applying laser light according to the preferred embodiment of the present invention

The laser device can optionally include optics for shaping the beam to create desired spot shapes, as described in U.S. Pat. No. 6,746,473 issued to Tucek and Shanks. In the preferred embodiment, laser energy is applied with a laser device capable of creating a linear spot shape. By using a line of laser light, the number of times the laser light must be scanned back and forth across the targeted area is minimized. FIG. 6 illustrates a laser device with optics for shaping the beam and creating a linear shape. As shown in FIG. 6, a laser device includes an optical arrangement 51 having a collimating lens 54 and a line generating prism 56 disposed in serial relation to the laser energy source 52. The collimating lens 54 and line generating prism 56 receive and transform the generated beam of laser light into a line of laser light L. As an alternative, a suitable electrical or mechanical arrangement or combination thereof could be substituted for or combined with the optical arrangement to achieve a desired spot shape.

Upper and lower laser devices 27 and 28 can also be laser scanning devices such as the inventions described in U.S. Published Patent Application 2006/0095099 belonging to Shanks and Tucek, which is incorporated herein by reference. By using laser scanning devices, the line generating prism can be operated to scan laser light in any pattern, as described in the U.S. Published Patent Application 2006/0095099.

Upper arm 17 and lower arm 18 also support feedback sensors 80 either separate from or as part of the upper and lower laser devices 27 and 28. The sensors 80 are preferably ultrasonic proximity sensors that will give vertical distance feedback regarding the distance between laser devices 27 and 28 and the patient's body. Along with the vertical distance feedback from feedback sensors 80, linear movement encoders track the horizontal movement of the laser devices. The combination permits three-dimensional movement of the laser devices to maximize the areas being treated. Moreover, by tracking the vertical distance of the laser devices in relation to the patient being irradiated with laser energy, an active scan can be accomplished. The laser devices 27 and 28 can be positioned as the patient is being treated with laser energy.

The laser guidance system 20, the laser devices 27 and 28, and the feedback sensors 80 can all be operated with a control system, which is partially or substantially located in control center 19. Control center 19 also preferably incorporates a display 19a and operator input device 19b such as a touch screen or a separate keyboard and screen. Using control center 19, the operator can select and input information relative to the treatment protocol, operation of the full-body scanner, and patient details. The control system is comprised of various discrete circuits, as is known in the art. For example, the control system includes control circuitry for operating the laser guidance system 20, the laser devices 27 and 28, and the sensors 80. In a further form, the control system includes a microprocessor programmed to operate in various modes. While the invention is not limited to any particular programmed operation mode, by way of example the following modes of operation are available:

1. The carriage assembly 16 is programmed to move linearly through a series of fixed regions and dwell for a pre-set period at each region for laser application by the upper and lower laser devices 27, 28 at the region or at a specific targeted area. The regions or specific targeted areas may be input by an operator or user to align with particular positions on the body that require treatment.
2. The vertical displacement of the upper and lower laser devices 27, 28 is programmed to move vertically through a series of fixed heights and dwell for a pre-set period at each region for laser application by the upper and lower laser devices 27, 28 at the region or at a specific targeted area. The regions or specific targeted areas may be input by an operator or user to align with particular positions on the body that require treatment.
3. The upper and lower laser devices 27, 28 are programmed to move through a series of fixed regions and dwell for a pre-set period at each region. The regions may be input by a user to align with particular positions on the body that require treatment.
4. The wavelength of applied laser energy is periodically changed by changing the operating laser diode in one or more of the upper and lower laser devices 27, 28 during a repetitive scan. This allows stimulation of the targeted area at multiple wavelengths.
5. The focal position of the beam shaping optics of one or more of the upper or lower laser devices 27, 28 is changed to generate smaller or large spot sizes on the targeted area.
6. The laser power of one or more of the upper and lower laser devices is varied.

FIG. 7 illustrates a second and preferred embodiment of scanner 10 where the patient support is a base 72 with a seat 74. As shown, the full-body laser scanner 10 also comprises one or more laser devices 71, a control center 19, and a laser guidance system that comprises a vertical stanchion 76, an orbital guide ring 77, and a carriage assembly 70. The second embodiment of scanner 10 can also optionally include feedback sensors 80. Vertical stanchion 76 is preferably connected to base 72 either directly or with an arm 75 that extends away from seat 74. Alternately, vertical stanchion 76 can be a standalone structure. Preferably, vertical stanchion 76 is in a fixed position such that it does not move when, for example, seat 74 moves or carriage assembly 70 moves.

Base 72 supports seat 74, and seat 74 can be any type of seat capable of supporting a patient who is sitting. The seat preferably accommodates a patient sitting facing stanchion 76, facing away from stanchion 76, or facing to one side or other. For example, a patient can sit on seat 74 shown in FIG. 7 with his back resting on the seat back 74a, with his chest resting on the seat back 74a, or with either of his shoulders or arms resting on the seat back 74a. Seat 74 also preferably pivots on base 72 and can be rotated manually or optionally rotated with a center mass rotational drive motor 73. The base and seat permit a patient to be treated on one more sides without realignment. For example, when a patient sits with his right shoulder on the seat back 74a, his front and back are exposed for laser treatment.

The laser guidance system of the second embodiment is an orbital guidance system comprising an orbital guide ring 77 and carriage assembly 70 as shown in FIG. 7. While only one orbital guide ring 77 and carriage assembly 70 is shown, any number of orbital guide rings and carriage assemblies can be used in any combination. For example, one carriage assembly may support two or more orbital guide rings. Likewise, multiple orbital guide rings may each be supported by a separate carriage assembly. The carriage assembly 70 translates on vertical stanchion 76 and comprises vertical movement drive motor 78. Motor 78 can be any drive motor capable of moving a structure up and down a vertical support or stanchion, as is known in the art. If multiple orbital guidance systems are desired, each can have a vertical stanchion or all of the orbital guidance systems can be supported by a single vertical stanchion, or any combination thereof. Carriage assembly 70 can house a battery, control circuitry, and any other components necessary to facilitate the carriage's movement along the stanchion 76. Carriage assembly 16 also can house any components necessary for operating any of lasers 71. Carriage assembly 70 also cooperates with control center 19, which can be physically, electrically, or wirelessly connected to carriage assembly 70.

Orbital guide ring 77 is connected to carriage assembly 70, and is directed towards seat 74 such that it forms a partial or full ring around a patient sitting on seat 74. Orbital guide ring 77 can be any type of substantially circular rails or guides capable of supporting a translating object, as is known in the art. Orbital guide ring 77 is either integral with carriage assembly 70 or otherwise rigidly secured to carriage assembly such that the movement of laser devices 71 along ring 77 are not impeded and such that as carriage assembly translates along stanchion 76, orbital guide ring 77 translates vertically as well.

Orbital guide ring 77 further supports one or more laser devices 71 that are directed inward toward the center of orbital guide ring 77. Preferably, laser devices 71 are aligned along the radius of orbital guide ring 77 such that the laser output location 71a is also aligned along the radius of orbital guide ring 77. Laser devices 71 can translate along guide ring 77 and are preferably driven by an orbital drive motor 79 connected to each of laser device 71. Motor 79 can be any drive motor capable of moving a structure along an orbital guide ring, as is known in the art. Preferably, each of the laser devices 71 are controlled by the control system as well as each of the orbital drive motors 79.

Laser devices 71 can be any laser device that provides low-level energy. For further information regarding laser devices 71, see the discussion above for upper laser devices 27 and lower laser devices 28. Also see the discussion above regarding beam-shaping optics and laser scanning devices, both of which apply to laser devices 71 as well.

Each laser device 71 can also support a feedback sensor 80 either separate from laser device 71 or as part of laser devices 71. As shown in FIG. 7, sensor 80 is positioned outside of laser device 71. Alternatively, it can be positioned within the same housing as laser device 71. The sensors 80 are preferably ultrasonic proximity sensors that will give distance feedback for the laser devices 27 and 28. Along with the distance feedback from feedback sensors 80, movement encoders track the movement of the laser devices. Additionally movement encoders track the vertical movement of the carriage assembly 70 and accordingly the orbital ring 77 and laser devices 71. The combination permits three-dimensional movement of the laser devices to maximize the areas being treated. Moreover, by tracking the distance of the laser devices in relation to the patient being eradiated with laser energy, an active scan can be accomplished. The laser devices can be positioned as the patient is being treated with laser energy. Ultrasonic proximity sensors and movement encoders are well known in the art.

In the laser guidance system shown in FIG. 7, each of the laser devices 71, and each of the feedback sensors 80 can all be operated with the control system, which is partially or substantially located in control center 19. Control center 19 is preferably mounted on a separate support 65 or alternatively is mounted on vertical stanchion 76, carriage assembly 70, base 72, or seat 74. As described above with respect to the first embodiment, control center 19 also preferably incorporates a display and operator input device, such as a touch screen, where the operator can select and input information relative to the treatment protocol, operation of the full-body scanner, and patient details. The control system is comprised of various discrete circuits, as is known in the art. For example, the control system includes control circuitry for operating the laser guidance system, each of the laser devices 71, and each of the sensors 80. In a further form, the control system includes a microprocessor programmed to operate in various modes as described above with respect to the first embodiment of this invention.

FIG. 8 illustrates a third embodiment of scanner 10 where the patient support is a base 82 and platform 84. As shown, the full-body laser scanner 10 comprises a base 82 with a platform 84, one or more laser devices 71, a control center 19, and an orbital laser guidance system that comprises a vertical stanchion 76, an orbital guide ring 77, and a carriage assembly 70. The third embodiment of scanner 10 can also optionally include feedback sensors 80 and movement encoders.

Base 82 supports platform 84, and platform 84 can be any type of structure capable of supporting a patient who is standing. The platform preferably accommodates a patient standing facing stanchion 76, facing away from stanchion 76, or facing to one side or other. Platform 84 also preferably pivots on base 82 and can be rotated manually or optionally rotated with a center mass rotational drive motor (not shown). The base and platform permit a patient to be treated on one more sides without realignment. For example, when a patient stands on the platform, his front and back are exposed for laser treatment.

The carriage assembly 70, orbital guide ring 77, laser devices 71, optional feedback sensors 80 and movement encoders, drive motors 78 and 79, and control system and control center 19 for the third embodiment of full body scanner 10 are described above with respect to the second embodiment of full body scanner 10.

Generally, to map and contour a patient's body with the full-body laser scanner 10, the patient is aligned on the patient support, and the laser devices and the feedback sensors are driven about the patient's body. With the control panel, an operator chooses whether to map, contour, or map and contour the patient's body. The operator can also choose any preprogrammed treatment protocols or can manually control the carriage's movement and the lasers. The carriage assembly and laser devices translate according to the chosen protocol or manual instructions. Additionally, the laser devices apply laser energy according to the chosen protocol or manual instructions, the feedback sensors give feedback regarding the distance between the laser devices, and the contours of the patient's body and the movement encoders track the location or position of the laser devices. Tracked movements of the laser devices along with distance measurements provided by the feedback sensors provide the data for creating a map of the patient's contours and identifying targeted areas of the body for laser treatment.

Using the first embodiment of the full-body laser scanner as an example, the patient lies, preferably on his back, on the bed of slats 14. With the control center 19, an operator chooses whether to map, contour, or simultaneously map and contour the patient's body. The operator can also choose any preprogrammed treatment protocols or can manually control the carriage assembly's 16 movement and lasers devices 27, 28. The carriage assembly 16 translates from one end of the base 12 and bed to the other in either one continuous translation or with several back and forth translations of various amounts. While the carriage assembly 16 translates, the upper arm 17 translates accordingly and upper laser devices 27 apply laser energy to the surfaces of the patient's body that are directed upwards. Simultaneously, the lower arm 18 translates accordingly and lower laser devices 28 apply laser energy to the surfaces of the patient's body that are directed downwards. Using the sensors 80, the full-body laser scanner 10 can collect reflected or backscattered ultrasound waves and process it along with information regarding the location of the laser devices 27, 28 to map the contours of the patient's body and identify targeted areas of the body for laser treatment. Alternatively, the operator can manually identify targeted areas of the body for laser treatment. If desired, upper laser devices 27 can be raised or lowered to apply laser energy to the surfaces of the patient's body that are directed upwards, and lower laser devices 28 can be raised or lowered to apply laser energy to the surfaces of the patient's body that are directed downwards. Next, low-level laser energy can be applied to the targeted areas of the patient's body to reduce cellulite and contour the body. Laser energy can also be applied according to treatment protocols for other laser applications.

For treating cellulite or contouring the body using low-level laser light, laser energy is applied to targeted areas of cellulite on a patient's body. The targeted areas of cellulite are made up of adipocyte tissue below the skin of the patient. Sufficient laser energy is applied to the adipocyte tissue through the skin to release at least a portion of the intracellular fat into the interstitial space. The released intracellular fat is then removed from the body through the body's normal systems, such as metabolic, lymphatic, or excretory systems. The procedure may be repeated in one or more additional areas to remove additional cellulite. Moreover, the procedure may be repeated one or more times at each targeted area over a period of days or weeks. The procedure reduces fat as well as cellulite.

Typically, fat leakage into the interstitial space is seen as early as 3-5 minutes of laser energy application. The preferred treatment is about 20 minutes of laser energy application, three times a week for about two weeks. Alternatively, applying twenty minutes of laser energy can be repeated over longer or shorter time periods, such as repeated treatments within forty-eight hours. The dosage of laser energy required to achieve release of the intracellular fat into the interstitial space will vary depending on the thickness of the patient's skin, thickness of fatty tissue, and other biological factors peculiar to each patient.

The mechanism involved in releasing the intracellular fat from the cells is believed to be the formation of a transitory pore in the cell membrane. Adipose tissue comprises normal fat cells wherein the cell membrane is filled with intracellular fat. Upon sufficient doses of low-level laser energy, the cell membrane is momentarily disrupted, releasing the intracellular fat. Upon cessation of the energy application, the pores close and the cell membrane returns to contiguity. The fat cell is not destroyed, provided the duration of laser treatment is appropriate. For a 635 nm laser of less than 1 W, treatments of less than about 12 minutes do not destroy cells.

Applying low level laser energy causes no immediate detectable temperature rise of the treated tissue and no macroscopically visible changes in tissue structure. Low level laser energy penetrates the skin and is specific to the depth of the desired zone of fat to be treated. Consequently, the treated and surrounding tissue is not heated and is not damaged. Preferably the laser light is visible to the human eye so that the area of application is easily determined. Also preferably, the laser energy is preferably applied by a scanning laser device, and the laser energy can be applied in a back and forth sweeping motion, in a rotary scanning motion, or in any other desirable pattern.

EXAMPLE 1

The targeted areas for fat reduction are the patient's abdomen and the back of the patient's thighs. The patient lays prone and face up on the slats 14 of the bed of the full-body scanner 10 of the first embodiment. The carriage assembly translates to position the upper arm 17 over the patient's abdomen. The patient's abdomen is then treated with laser energy, using a 635 nm semiconductor diode laser with maximum power of 1 W. The laser energy is applied for 12 minutes at the targeted fat areas without touching the patient. The carriage assembly 16 next translates to position the lower arm 18 under the back of the patient's thighs. The back of the patient's thighs are then treated with laser energy, using a 635 nm semiconductor diode laser with maximum power of 1 W. The laser energy is applied for 12 minutes at the targeted fat areas without touching the patient.

EXAMPLE 2

The patient lays prone and face up on the slats 14 of the bed of the full-body scanner 10 of the first embodiment. The carriage assembly 16 translates from one end of the scanner 10 to the other. The patient's body is mapped using ultrasonic sensors 80 that give device height feedback relative to the patient's body surface and linear movement encoders. The collected data is collected and processed, and targeted treatment areas for fat reduction are identified. The targeted areas for fat reduction are the patient's abdomen and the back of the patient's thighs. The patient remains prone and face up on the transparent bed of the full-body scanner. The carriage assembly 16 translates to position the upper arm 17 over the patient's abdomen. The upper laser devices 27 are lowered to reduce the distance between the upper laser devices and the patient's abdomen. The patient's abdomen is then treated with laser energy, using a 635 nm semiconductor diode laser with maximum power of 1 W. The laser devices 27, 28 are scanning laser devices capable of emitting laser energy in a rotary scanning motion and laser energy is applied for 12 minutes in a rotary scanning motion at the targeted fat areas without touching the patient. The scanning motion results from micromanipulating scanning heads in the upper laser devices. The carriage assembly next translates to position the lower arm 18 under the back of the patient's thighs. The lower laser devices 28 are raised to reduce the distance between the lower laser devices and the patient's thighs. The back of the patient's thighs are then treated with laser energy, using a 635 nm semiconductor diode laser with maximum power of 1 W. The laser energy is applied for 12 minutes in a rotary scanning motion at the targeted fat areas without touching the patient. The scanning motion results from micromanipulating scanning heads in the lower laser devices.

EXAMPLE 3

The patient sits on seat 74 of the second embodiment of the full body scanner 10 with his back to vertical stanchion 76. The targeted area for fat reduction are the patient's waist. The carriage assembly 70 translates to position the orbital guide ring 77 near the upper part of the patient's waist, and the laser devices 71 are positioned according to feed back from the ultrasonic sensors 80 and movement encoders. The patient's waist is then treated with laser energy, using a 635 nm semiconductor diode laser with maximum power of 1 W. The laser energy is applied for 12 minutes in a rotary scanning motion at the targeted fat areas without touching the patient. The scanning motion results from micromanipulating scanning laser heads in the laser devices 71. The carriage assembly 70 next translates to another position of the patient's waist, and the laser devices 71 are positioned according to feed back from the ultrasonic sensors 80 and linear movement encoders. The patient's waist is again treated with laser energy, using a 635 nm semiconductor diode laser with maximum power of 1 W. The laser energy is applied for 12 minutes in a rotary scanning motion at the targeted fat areas without touching the patient. The scanning motion results from micromanipulating scanning laser heads in the laser devices 71.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

We claim:

1. A laser scanning device comprising:
   a. a patient support configured to align a patient, the support configured to enable all of the patient's sides to be exposed for treatment by one or more laser devices, without repositioning the patient;
   b. a laser guidance system;
   c. one or more laser devices moveably attached to the laser guidance system and directed toward a patient supported on the patient support; and
   d. a control system operably connected to the laser guidance system.

2. The laser scanning device of claim 1 further comprising feedback sensors moveably attached to the laser guidance system and directed toward a patient supported on the patient support.

3. The laser scanning device of claim 2 wherein the control system is operably connected to the laser devices, the feedback sensors, and the laser guidance system.

4. The laser scanning device of claim 1 wherein the control system is operably connected to the laser devices and the laser guidance system.

5. The laser scanning device of claim 1 wherein the laser guidance system is an orbital guidance system.

6. The laser scanning device of claim 5 wherein the orbital guidance system comprises a carriage assembly and an orbital guide ring attached to the carriage assembly and wherein the laser devices are moveably attached to the orbital guide ring.

7. The laser scanning device of claim 6 further comprising a vertical stanchion offset from the patient support, the carriage assembly being moveably attached to the vertical stanchion.

8. The laser scanning device of claim 7 wherein the carriage assembly further comprises a drive motor positioned to drive the carriage assembly vertically along with the vertical stanchion.

9. The laser scanning device of claim 5 wherein each laser device further comprises a drive motor positioned to drive each laser device about the orbital guidance system, and wherein the control system is operably connected to each of the laser devices, the orbital guidance system, and the drive motor.

10. The laser scanning device of claim 9 wherein the patient support is a chair.

11. The laser scanning device of claim 9 wherein the patient support is a platform.

12. The laser scanning device of claim 1 wherein the laser guidance system is a linear guidance system.

13. The laser scanning device of claim 12 wherein the linear guidance system comprises a carriage assembly and a first arm attached to the carriage assembly and wherein at least one of the first laser devices is moveably attached to the first arm.

14. The laser scanning device of claim 13 wherein the device comprises a plurality of laser devices, wherein the linear guidance system further comprises a second arm attached to the carriage assembly, and wherein at least one of the laser devices is moveably attached to the second arm.

15. The laser scanning device of claim 14 wherein the linear guidance system further comprises one or more first feedback sensors moveably attached to the first arm and one or more second feedback sensors moveably attached to the second arm.

16. The laser scanning device of claim 15 wherein the patient support is a bed, wherein the patient support further comprises a carriage rail parallel to the bed, the carriage assembly being moveably attached to the carriage rail, and wherein the first arm is positioned above the bed and the second arm is positioned below the bed.

17. The laser scanning device of claim 15 wherein the control system is operably connected to the carriage assembly, the laser devices, and the feedback sensors.

18. A method for mapping and treating a patient's contours comprising:
  a. placing the patient on a full body scanning device comprising:
    i. a patient support configured to align a patient with all of the patient's sides exposed for treatment by one or more laser devices, without repositioning the patient;
    ii. a laser guidance system;
    iii. one or more laser devices moveably attached to the laser guidance system and directed toward a patient supported on the patient support;
    iv. one or more feedback sensors moveably attached to the laser guidance system and directed toward a patient supported on the patient support; and
    v. a control system operably connected to the laser guidance system; and
  b. operating the full body scanning device with the control system.

19. The method of claim 18 further comprising recording feedback about the contours of the patient's body provided by the feedback sensors.

20. The method of claim 18 further comprising applying laser energy to the patient's body.

\* \* \* \* \*